United States Patent
Spiro et al.

(10) Patent No.: US 7,037,175 B1
(45) Date of Patent: May 2, 2006

(54) METHOD OF SHARPENING CUTTING EDGES

(75) Inventors: Clifford Spiro, Naperville, IL (US); George Steuer, Aurora, IL (US); Frank Kaufman, Geneva, IL (US)

(73) Assignee: Cabot Microelectronics Corporation, Aurora, IL (US)

( * ) Notice: Subject to any disclaimer, the term of this patent is extended or adjusted under 35 U.S.C. 154(b) by 0 days.

(21) Appl. No.: 10/968,571

(22) Filed: Oct. 19, 2004

(51) Int. Cl.
*B24B 3/00* (2006.01)

(52) U.S. Cl. ............................................. 451/45; 76/82
(58) Field of Classification Search ................. 451/36, 451/43, 45, 59, 60, 917; 76/82, 82.2
See application file for complete search history.

(56) References Cited

U.S. PATENT DOCUMENTS

| | | | |
|---|---|---|---|
| 4,122,602 A * | 10/1978 | Sastri et al. ............... 30/346.5 |
| 4,122,603 A | 10/1978 | Sastri |
| RE29,989 E | 5/1979 | Polk et al. |
| 4,305,779 A | 12/1981 | Steeves et al. |
| 5,230,833 A | 7/1993 | Romberger et al. |
| 5,295,305 A | 3/1994 | Hahn et al. |
| 5,785,586 A * | 7/1998 | Delsignore ................. 451/556 |
| 5,983,756 A | 11/1999 | Orloff |
| 6,330,750 B1 | 12/2001 | Meckel |
| 6,379,858 B1 | 4/2002 | Perry et al. |
| 6,488,834 B1 | 12/2002 | Francis |
| 2002/0083598 A1 * | 7/2002 | Julien ........................... 30/350 |
| 2002/0106978 A1 | 8/2002 | Michaud et al. |
| 2002/0142182 A1 | 10/2002 | Peker et al. |
| 2003/0148716 A1 * | 8/2003 | Lyons, III .................... 451/45 |
| 2004/0099120 A1 | 5/2004 | Yamada et al. |

FOREIGN PATENT DOCUMENTS

| | | |
|---|---|---|
| EP | 0 139 169 A2 | 5/1985 |
| EP | 0 139 169 A3 | 5/1985 |
| GB | 515922 | 12/1939 |
| GB | 718941 | 11/1954 |
| GB | 1106071 | 3/1968 |
| GB | 1350594 | 4/1974 |
| GB | 1544129 | 4/1979 |
| GB | 1544130 | 4/1979 |
| WO | WO 01/68290 A1 | 9/2001 |
| WO | WO 02/100611 A2 | 12/2002 |

* cited by examiner

*Primary Examiner*—Jacob K. Ackun, Jr.
(74) *Attorney, Agent, or Firm*—Francis Koszyk

(57) ABSTRACT

The invention is directed to a method for polishing a cutting edge on a cutting instrument, comprising contacting a cutting edge of a cutting instrument with a polishing pad and a chemical-mechanical polishing composition comprising particles of an abrasive, and a liquid carrier, wherein the abrasive is suspended in the liquid carrier, and abrading at least a portion of the cutting edge to polish the cutting edge. The invention further provides a cutting instrument having a highly uniform edge.

21 Claims, 4 Drawing Sheets

METHOD OF SHARPENING CUTTING EDGES

FIELD OF THE INVENTION

This invention pertains to a cutting instrument and a method for making the same.

BACKGROUND OF THE INVENTION

Generally, cutting edges on cutting instruments are manufactured by processing an appropriate feedstock having a thickness that diminishes from the beginning of the cutting edge to the ultimate edge so as to provide a cutting edge. Conventional cutting-edge forming processes typically involve grinding operations that remove material in a gradient beginning at a distance from the ultimate edge to the ultimate edge itself. The process of grinding generally involves contacting the feedstock with hard abrasive particles imbedded in a grinding wheel rotating about an axis, thereby mechanically abrading material from the feedstock. This grinding operation often is carried out with large abrasive particles that tend to leave large gouges in the surface of the cutting edge. Subsequent processes of honing and stropping are then used to reduce the depth of gouges on the cutting edge surface. Honing and stropping are both mechanical processes that remove the softer material of the cutting edge by abrasion by the harder material of the abrasive.

A cutting edge may be characterized in several ways. First, the thickness of the cutting edge at the ultimate edge determines in part the "sharpness" of the cutting edge. A thinner cutting edge will generally encounter less resistance in parting of the material being cut. Another parameter impacting the performance of a cutting instrument is the smoothness and the contour of the cutting edge and of the sides of the cutting edge extending back towards the feedstock comprising the body of the cutting instrument. An irregular contour will lead to small, even microscopic, points that penetrate the material being cut before other parts of the cutting edge encounter the substrate. This leads to some degree of tearing rather than slicing. A cutting edge having a rough surface on the sides of the cutting edge will abrade, or tear, material that passes over the sides of the cutting edge, as the material must be pushed aside to allow for passage of the cutting edge through the material being cut.

In the surgical arts, where the material being cut is living tissue, a sharp and smooth cutting edge in, for example, surgical scalpels, is of paramount interest. The making of an incision in living tissue results in trauma to that tissue, due to the work that must be imparted to the tissue in making the incision. The work required to pass a scalpel through tissue results from many factors, including edge sharpness, force applied to the blade, drag force acting on the sides of the blade, and the like. The trauma caused to tissue from an incision results in increased time required for healing, increased chance for infection, a limitation to the size of physiological structures that can be incised accurately, and unsightly scarring.

In this regard, many efforts have been made to improve the performance of cutting instruments, particularly of surgical instruments such as scalpels. For example, resort has been made to cutting instruments fabricated from diamonds, rubies, and sapphires, which are very hard materials and can be fabricated with edges that are very thin. However, these materials are very expensive and difficult to fabricate. Their hardness is actually a disadvantage in medical operations, as they tend to fracture upon encountering hard structures such as bone, thus potentially leaving fragments in the operative subject. Metals are economically processed into surgical scalpels and the like. However, difficulties with achieving sharp and smooth edges have led to efforts such as coating of cutting edges with friction-reducing materials to reduce trauma resulting from incisions.

The heightened requirements for cutting properties of surgical instruments due to the widespread introduction into clinical practice of new procedures for performing operations on vital organs and the development of microsurgical techniques have led to demands for improved methods of producing cutting instruments and improved cutting instruments themselves.

The invention provides such a method for producing improved cutting instruments and provides improved cutting instruments themselves. These and other advantages of the invention, as well as additional inventive features, will be apparent from the description of the invention provided herein.

BRIEF SUMMARY OF THE INVENTION

The invention is directed to a method for polishing a cutting edge on a cutting instrument, comprising (i) providing a cutting instrument having a cutting edge, (ii) contacting the cutting edge with a polishing pad and a chemical-mechanical polishing composition comprising (a) particles of an abrasive, and (b) a liquid carrier, wherein the abrasive is suspended in the liquid carrier, (iii) moving the polishing pad relative to the cutting edge with the chemical-mechanical polishing composition therebetween, and (iv) abrading at least a portion of the cutting edge to polish the cutting edge.

The invention further provides a cutting instrument, comprising a cutting instrument body having two flat faces and a direction of elongation and defining an ultimate edge, and having at least one cutting edge extending parallel to the direction of elongation, wherein a maximum deviation from a line defined by two points on the ultimate edge of the cutting edge separated by 5000 µm of any point on the ultimate edge of the cutting edge between the two points is about 4 µm or less.

The invention also provides a cutting instrument, comprising a cutting instrument body having two flat faces and a direction of elongation and defining an ultimate edge, and having at least one cutting edge extending parallel to the direction of elongation, wherein a maximum deviation from a line defined by two points on the ultimate edge of the cutting edge separated by 750 µm of any point on the ultimate edge of the cutting edge between the two points is about 1 µm or less.

DETAILED DESCRIPTION OF THE INVENTION

The invention provides a method for polishing a cutting edge on a cutting instrument. The method involves (i) providing a cutting instrument having a cutting edge, (ii) contacting the cutting edge with a polishing pad and a chemical-mechanical polishing composition comprising (a) particles of an abrasive and (b) a liquid carrier, wherein the abrasive is suspended in the liquid carrier, (iii) moving the polishing pad relative to the cutting edge with the chemical-mechanical polishing composition therebetween, and (iv) abrading at least a portion of the cutting edge to polish the cutting edge.

The cutting instrument can be any cutting instrument and typically comprises a cutting instrument body having two flat faces and a direction of elongation, and having at least one cutting edge extending parallel to the direction of elongation. Examples of cutting instruments suitable for polishing by the inventive method include but are not limited to knives, surgical scalpels, scissors, and razors. The cutting instrument can have any suitable additional features, for example, a separate handle attached to the cutting instrument by suitable means.

Figure 1:
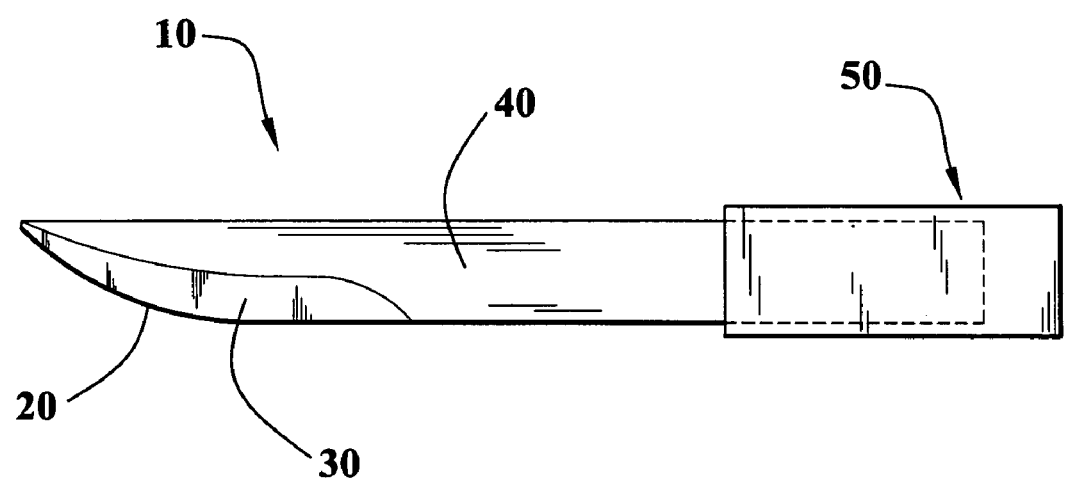
FIG. 1 is a side view of a cutting instrument in accordance with the invention.

Shown in FIG. 1 is a side view of a cutting instrument (10) of the invention. In general any cutting instrument has a body (40) and a cutting edge (30). In such cutting instruments the cutting edge is defined as that portion of the cutting instrument which tapers to a terminating, or ultimate edge (20). The body (40) of the cutting instrument is defined as the structure that transfers an applied load from the cutting instrument driving force to the ultimate edge (20) of the cutting edge (30). In addition, as shown in FIG. 1, a cutting instrument can include an optional handle or grip (50) which serves as a stable interface between the cutting instrument user and the cutting instrument.

The cutting edge can be integral with the cutting instrument body. A cutting edge can be formed directly on a cutting instrument body, thus comprising the same material as the cutting instrument body. The cutting edge can be non-integral with the cutting instrument body and can be formed by layering a second material on the first material of the cutting instrument body.

The cutting instrument and cutting edge can comprise any suitable material. Typically, the cutting instrument and cutting edge comprise a metal. For example, the metal can be a metal alloy, e.g., an alloy of iron with at least one element selected from the group consisting of carbon, chromium, nickel, and cobalt. Preferred alloys of iron include stainless steels and carbon steels. The cutting instrument and cutting edge can comprise any stainless steel or carbon steel. Stainless steels are typically comprised of iron and chromium in various proportions, although other elements, including silicon, nickel, molybdenum, phosphorus, sulfur, copper, and aluminum, are often components of commercially available stainless steels. Carbon steels typically comprise iron and carbon, and can include additional elements, including chromium, nickel molybdenum, vanadium, and silicon. Carbon steels are typically further classified as mild steels, comprising less than about 0.25 wt. % carbon, medium carbon steels, comprising about 0.25 wt. % to about 0.45 wt. % carbon, and high carbon steels, comprising about 0.45 wt. % to about 1.5 wt. % carbon.

The metal can be any suitable bulk amorphous alloy. Generally, bulk amorphous alloys are formed by solidification of alloy melts by cooling the alloy to a temperature below its glass transition temperature before appreciable homogeneous nucleation and crystallization has occurred. Many bulk amorphous alloys are known in the art, all of which are suitable for use in the cutting instrument of the invention.

The cutting edge can comprise a non-metal, such as diamond or sapphire. Any suitable cutting edge comprising diamond or sapphire can be polished by the inventive polishing method.

The cutting edge can be formed by any suitable method. Conventional methods of grinding, honing, and stropping can be used to prepare a cutting edge before application of the inventive polishing method. However, an unfinished cutting edge body can be subjected to the inventive polishing method without any prior fabrication steps.

The cutting edge is contacted with a polishing pad and a chemical-mechanical polishing composition. The polishing pad (e.g., polishing surface) can be any suitable polishing pad, many of which are known in the art. Suitable polishing pads include, for example, woven and non-woven polishing pads. Moreover, suitable polishing pads can comprise any suitable polymer of varying density, hardness, thickness, compressibility, ability to rebound upon compression, and compression modulus. Suitable polymers include, for example, polyvinylchloride, polyvinylfluoride, nylon, fluorocarbon, polycarbonate, polyester, polyacrylate, polyether, polyethylene, polyamide, polyurethane, polystyrene, polypropylene, coformed products thereof, and mixtures thereof.

The polishing pad can have any suitable configuration. For example, the polishing pad can be circular and when in use have a rotational motion about an axis perpendicular to the plane defined by the surface of the pad. The polishing pad can be cylindrical, the surface of which acts as the polishing surface, and when in use have a rotational motion about the central axis of the cylinder. The polishing pad can be in the form of an endless belt, which when in use has a linear motion with respect to the cutting edge being polished. The polishing pad can have any suitable shape, and when in use have a reciprocating or orbital motion along a plane or a semicircle. Many other variations will be readily apparent to the skilled artisan.

The chemical-mechanical polishing composition comprises particles of an abrasive and a liquid carrier, wherein the abrasive is suspended in the liquid carrier. The abrasive can be any suitable abrasive and preferably is selected from the group consisting of silica, alumina, ceria, titania, zirconia, germania, diamond, polycarbonate, silicon carbide, titanium carbide, titanium nitride, niobium carbide, chromium carbide, and mixtures thereof. More preferably, the abrasive is silica.

The silica can be any suitable form of silica. Suitable forms of silica include fumed silica and colloidal silica. Fumed silica is typically prepared by a pyrogenic process, in which a suitable precursor, such as silicon tetrachloride, undergoes vapor phase hydrolysis at high temperatures. Colloidal silica useful in the context of the invention includes wet-process type silica particles (e.g., condensation-polymerized silica particles). Condensation-polymerized silica particles typically are prepared by condensing $Si(OH)_4$ to form colloidal particles, where colloidal is defined as having an average particle size between about 1 nm and about 1000 nm. Such abrasive particles can be prepared in accordance with U.S. Pat. No. 5,230,833 or can be obtained as any of various commercially available products, such as the Akzo-Nobel Bindzil 50/80 product and the Nalco 1050, 2327, and 2329 products, as well as other similar products available from DuPont, Bayer, Applied Research, Nissan Chemical, and Clariant.

The abrasive particles typically have an average particle size (e.g., average particle diameter) of about 20 nm to about 500 nm. Preferably, the abrasive particles have an average particle size of about 70 nm to about 300 nm (e.g., about 100 nm to about 200 nm).

The abrasive can be present in any suitable amount. Typically, about 0.001 wt. % or more abrasive (e.g., about 0.01 wt. % or more) can be present in the polishing composition. The amount of abrasive in the polishing composition preferably will not exceed about 40 wt. %, and more preferably will not exceed about 20 wt. % (e.g., will not exceed about 10 wt. %). Even more preferably, the amount of the abrasive will be about 0.01 wt. % to about 10 wt. % of the polishing composition.

The abrasive is suspended in the polishing composition, more specifically in the liquid carrier of the polishing composition. The abrasive preferably is colloidally stable. The term colloid refers to the suspension of abrasive particles in the liquid carrier. Colloidal stability refers to the maintenance of that suspension over time. In the context of this invention, an abrasive is considered colloidally stable if, when the abrasive is placed into a 100 ml graduated cylinder and allowed to stand unagitated for a time of 2 hours, the difference between the concentration of particles in the bottom 50 ml of the graduated cylinder ([B] in terms of g/ml) and the concentration of particles in the top 50 ml of the graduated cylinder ([T] in terms of g/ml) divided by the initial concentration of particles in the abrasive composition ([C] in terms of g/ml) is less than or equal to 0.5 (i.e., $\{[B]-[T]\}/[C] \leqq 0.5$). The value of [B]−[T]/[C] desirably is less than or equal to 0.3, and preferably is less than or equal to 0.1.

The chemical-mechanical polishing composition optionally further comprises an oxidizing agent. Without wishing to be bound by any particular theory, it is believed that the oxidizing agent reacts with the surface of the cutting edge to form a soft oxidized film that is easily abraded by suspended abrasive particles. The oxidizing agent can be any suitable oxidizing agent. Preferably, the oxidizing agent is selected from the group consisting of bromates, bromites, chlorates, chlorites, ferric nitrate, hydrogen peroxide, hypochlorites, iodates, monoperoxy sulfate, monoperoxy sulfite, monoperoxyphosphate, monoperoxyhypophosphate, monoperoxypyrophosphate, organo-halo-oxy compounds, periodates, permanganate, and peroxyacetic acid. A preferred example of an oxidizing agent is hydrogen peroxide. As will be appreciated by one of ordinary skill in the art, the choice of the oxidizing agent will depend on the material comprising the cutting edge.

The polishing composition can comprise any suitable amount of the oxidizing agent. Typically, the polishing composition comprises about 0.1 wt. % or more (e.g., about 0.2 wt. % or more, about 0.5 wt. % or more, or about 1 wt. % or more) oxidizing agent, based on the weight of the liquid carrier and any components dissolved or suspended therein. The polishing composition preferably comprises about 20 wt. % or less (e.g., about 15 wt. % or less, or about 10 wt. % or less) oxidizing agent, based on the weight of the liquid carrier and any components dissolved or suspended therein.

The liquid carrier can be any suitable liquid carrier. The purpose of the liquid carrier is to facilitate the application of the components of the polishing composition to the substrate surface to be polished. Typically, the liquid carrier is water, a mixture of water and a suitable water-miscible solvent, or an emulsion. Preferably, the liquid carrier comprises, consists essentially of, or consists of water, more preferably deionized water.

The chemical-mechanical polishing composition can have any suitable pH. Typically, the polishing composition will have a pH of about 12 or less (e.g., about 11 or less, or about 10 or less). Preferably, the polishing composition will have a pH of about 1 or more (e.g., about 2 or more, or about 3 or more).

The pH of the polishing composition can be achieved and/or maintained by any suitable means. More specifically, the polishing composition can further comprise a pH adjustor, a pH buffering agent, or a combination thereof. The pH adjustor can be any suitable pH-adjusting compound. For example, the pH adjustor can be potassium hydroxide, sodium hydroxide, ammonium hydroxide, or a combination thereof. The pH buffering agent can be any suitable buffering agent, for example, phosphates, acetates, borates, ammonium salts, and the like. The chemical-mechanical polishing composition can comprise any suitable amount of a pH adjustor and/or a pH buffering agent, provided such amount is sufficient to achieve and/or maintain the pH of the polishing system within the ranges set forth herein.

The chemical-mechanical polishing composition optionally further comprises one or more other additives. Such additives include any suitable surfactant and/or rheological control agent, including viscosity enhancing agents and coagulants (e.g., polymeric rheological control agents, such as, for example, urethane polymers), acrylates comprising one or more acrylic subunits (e.g., vinyl acrylates and styrene acrylates), and polymers, copolymers, and oligomers thereof, and salts thereof. Suitable surfactants include, for example, cationic surfactants, anionic surfactants, anionic polyelectrolytes, nonionic surfactants, amphoteric surfactants, fluorinated surfactants, mixtures thereof, and the like.

The chemical-mechanical polishing composition optionally further comprises an antifoaming agent. The antifoaming agent can be any suitable anti-foaming agent. Suitable antifoaming agents include, but are not limited to, silicon-based and acetylenic diol-based antifoaming agents. The amount of anti-foaming agent present in the polishing composition typically is about 40 ppm to about 140 ppm.

The chemical-mechanical polishing composition optionally further comprises a biocide. The biocide can be any suitable biocide, for example an isothiazolinone biocide. The amount of biocide used in the polishing composition typically is about 1 to about 50 ppm, preferably about 10 to about 20 ppm.

The cutting edge can be polished by any suitable technique. In a preferred method of chemically-mechanically polishing a cutting edge, the cutting edge typically will be pressed against a polishing pad in the presence of a polishing composition under controlled chemical, pressure, velocity, and temperature conditions. The preferred method of chemically-mechanically polishing a cutting edge is particularly suited for use in conjunction with a chemical-mechanical polishing (CMP) apparatus. Typically, the apparatus comprises a platen, which, when in use, is in motion and has a velocity that results from orbital, linear, or circular motion, a polishing pad in contact with the platen and moving with the platen when in motion, and a carrier that holds a substrate to be polished by contacting and moving relative to the surface of the polishing pad. The cutting instrument having a cutting edge can be mounted in a carrier that is adjustable with respect to the angle at which the cutting edge contacts the polishing pad. The polishing of the substrate takes place by the cutting edge being placed in contact with the polishing pad and the polishing composition of the invention and then the polishing pad moving relative to the cutting edge (with the polishing composition therebetween), so as to abrade at least a portion of the cutting edge to polish the cutting edge.

The chemical-mechanical polishing composition can be formulated prior to delivery to the polishing pad or to the surface of the cutting edge. The polishing composition can also be formulated (e.g., mixed) on the surface of the polishing pad or on the surface of the cutting edge, through delivery of the components of the polishing composition from two or more distinct sources, whereby the components of the polishing composition meet at the surface of the polishing pad or at the surface of the cutting edge. In this regard, the flow rate at which the components of the polishing composition are delivered to the polishing pad or to the surface of the cutting edge (i.e., the delivered amount of the particular components of the polishing composition) can be altered prior to the polishing process and/or during the polishing process, such that the polishing selectivity and/or viscosity of the polishing composition is altered. Moreover, it is suitable for the particular components of the polishing composition being delivered from two or more distinct sources to have different pH values, or alternatively to have substantially similar, or even equal, pH values, prior to delivery to the surface of the polishing pad or to the surface of the cutting edge. It is also suitable for the particular components being delivered from two or more distinct sources to be filtered either independently or to be filtered jointly (e.g., together) prior to delivery to the surface of the polishing pad or to the surface of the cutting edge.

The inventive method further provides an optional additional step of coating the cutting edge with a protective and/or strengthening coating after polishing the cutting edge. A protective and/or friction reducing layer of, for example, polytetrafluoroethylene, silicones, polyethylene, etc., can be applied to the cutting edge after the polishing operation. Strengthening coatings can be applied. A non-limiting example of a strengthening coating comprises a coating formed by application to the cutting edge of a molybdenum layer as a diffusion barrier, followed by deposition of diamond-like carbon. Another example of a strengthening coating is titanium nitride. Other examples of post-polishing coatings will be readily apparent to those skilled in the art.

Figure 2:
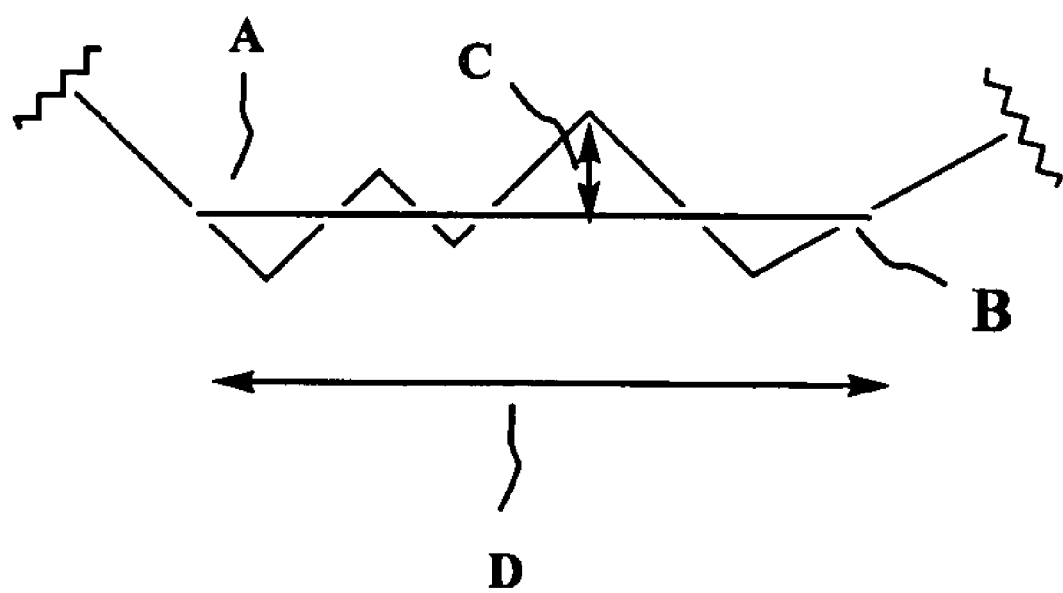
FIG. 2 is a schematic drawing illustrating the method used to characterize the contour of a cutting edge.

The inventive method is capable of producing an extremely even cutting edge. Typically, scanning electron microscopy of conventional cutting edges shows that, when examined at an angle perpendicular to the plane defined by the cutting instrument body upon which is formed the cutting edge, the ultimate edge of the cutting edge comprises an uneven contour. Points along the ultimate edge of the cutting edge will have a deviation from a line defined by two points on the ultimate edge of the cutting edge. The magnitude of the deviation will typically increase as the distance between the two points of the ultimate edge of the cutting edge defining the line used as a reference for the measurement increases. With reference to FIG. 2, the parameter used to characterize the contour of the ultimate edge of the cutting edge is the deviation between (a) a line D drawn between two points A, B on the ultimate edge and (b) a point C on the actual ultimate edge between the aforesaid two points A, B. Conventional cutting instruments have an ultimate edge that typically will have a minimum deviation from a line defined by two points on the ultimate edge separated by 5000 µm of any point on the ultimate edge between the two points of about 5 µm or greater. Similarly, for conventional cutting edge instruments, the minimum deviation from a line defined by two points on the ultimate edge separated by 750 µm of any point on the ultimate edge between the two points is about 2 µm or greater and/or the minimum deviation from a line defined by two points on the ultimate edge separated by 10 µm of any point on the ultimate edge between the two points is about 1.5 µm or greater.

A cutting edge polished by the inventive method shows a significantly more uniform or even contour of the ultimate edge when examined by scanning electron microscopy as discussed above than cutting edges produced by conventional practices. Typically, a cutting edge formed along a cutting instrument body, wherein the cutting instrument body comprises an alloy of iron with at least one element selected from the group consisting of carbon, chromium, nickel, and cobalt, when polished by the inventive method, will have a maximum deviation from a line defined by two points on the ultimate edge separated by 5000 µm of any point on the conventional ultimate edge between the two points is about 4 µm or less (e.g., about 3.5 µm or less, or about 3 µm or less, or even about 2.5 µm or less). The maximum deviation from a line defined by two points on the ultimate edge polished by the inventive method separated by 750 µm of any point on the ultimate edge between the two points is about 1 µm or less (e.g., about 0.9 µm or less, or about 0.8 µm or less, or even about 0.7 µm or less), and the maximum deviation from a line defined by two points on the ultimate edge separated by 10 µm of any point on the ultimate edge between the two points is about 0.5 µm or less (e.g., about 0.4 µm or less, or about 0.3 µm or less).

Figure 3:
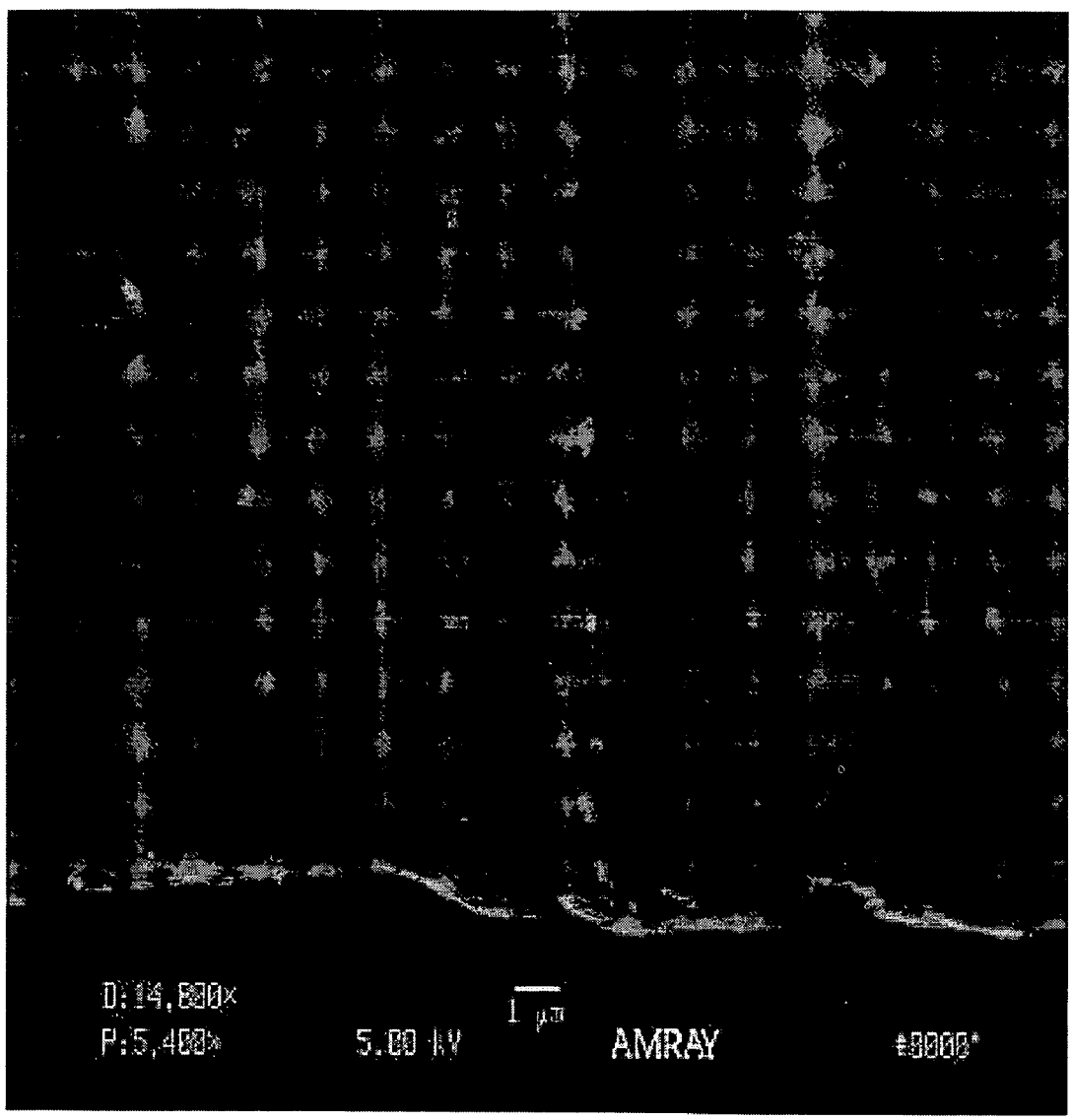
FIG. 3 is a scanning electron micrograph of a commercially available surgical blade as supplied by the manufacturer.

FIG. 3 is a scanning electron micrograph of a typical example of a commercially available surgical scalpel intended for harvesting skin grafts from humans. The viewing angle is perpendicular to the plane of the scalpel, with the ultimate edge of the cutting edge at the lower end of the illustration. Apparent from the illustration is the irregular contour of the cutting edge and its ultimate edge. Further, the flat side defining the edge of the scalpel is seen to feature ridges and pits.

Figure 4:
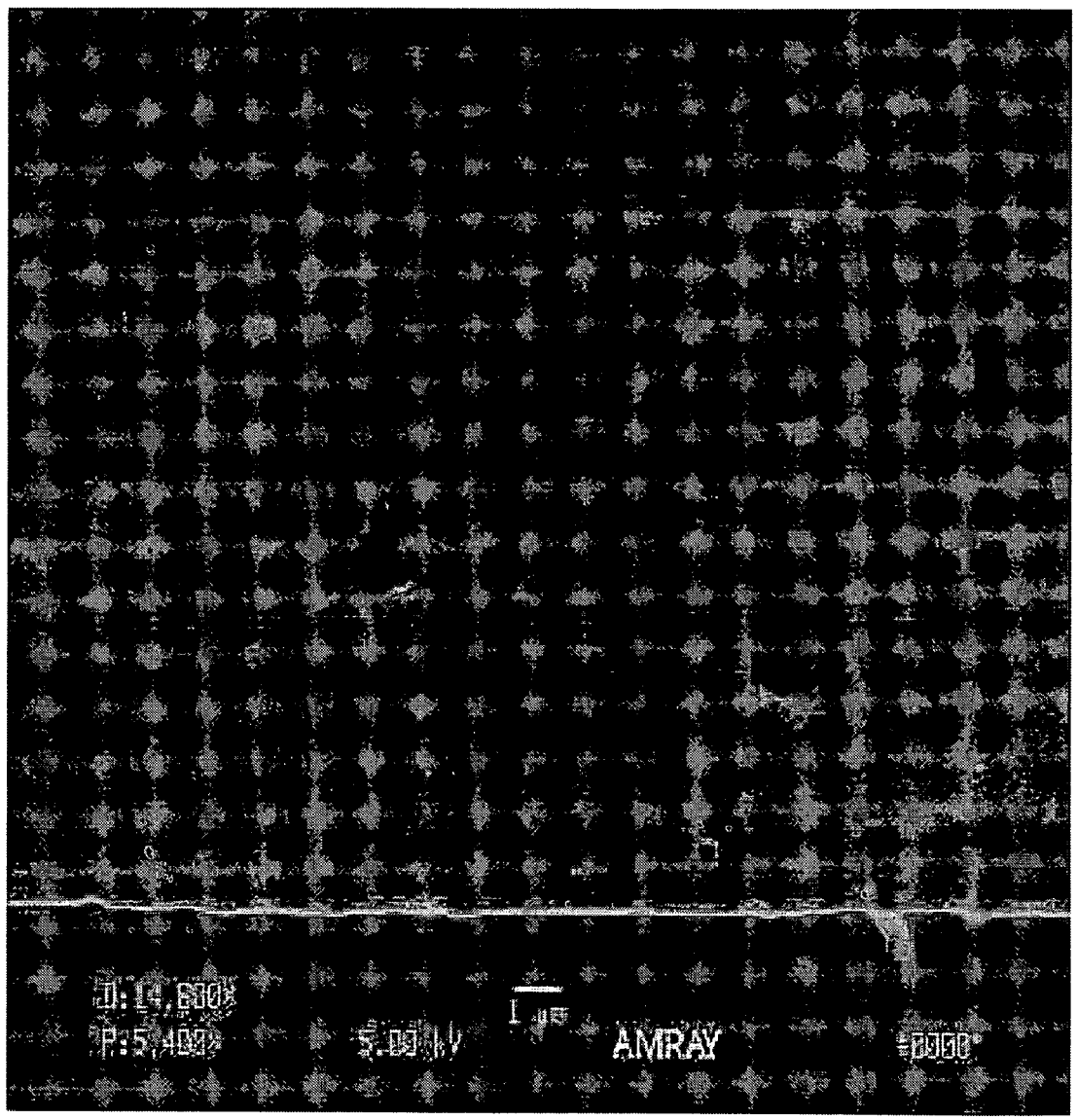
FIG. 4 is a scanning electron micrograph of the surgical blade illustrated in FIG. 3 after polishing in accordance with the inventive method.

A scanning electron micrograph of the same surgical scalpel of FIG. 3 after polishing by the inventive method is shown in FIG. 4. As is apparent from FIG. 4, the contour of the cutting edge and its ultimate edge is significantly more regular than the contour shown in FIG. 3.

Advantageously, the inventive method provides a cutting edge (30) as shown in FIG. 1 having surfaces defining the cutting edge that have significantly reduced surface roughness than can be achieved using conventional polishing techniques. Surface roughness is a measure of the depth of surface variations and a number of methods are well known in the art to determine surface roughness. The surface roughness can be measured mechanically by moving a stylus along a surface or by using light scattering techniques. The American Society of Mechanical Engineers (ASME) standard B46.1-2002 contains descriptions of methods used to measure and express surface roughness. The reduction in surface roughness achievable by the inventive method is apparent by visual comparison of FIG. 3 and FIG. 4.

Any cutting instrument can be polished using the inventive method. The cutting instrument will have (a) a cutting instrument body having two flat faces and a direction of elongation and (b) at least one cutting edge extending parallel to the direction of elongation. Non-limiting examples of cutting instruments suitable for polishing by the inventive method includes knives, scalpels, and scissors. Typically, a suitable cutting instrument for polishing by the inventive method comprises a knife. Preferably, the cutting instrument is a surgical scalpel.

Thus, the invention provides a cutting instrument comprising a cutting instrument body having two flat faces and a direction of elongation, and having at least one cutting edge extending parallel to the direction of elongation, wherein a maximum deviation from a line defined by two points on the ultimate edge of the cutting edge separated by 5000 µm of any point on the ultimate edge of the cutting edge between the two points is about 4 µm or less (e.g., about 3.5 µm or less, or about 3 µm or less, or even about 2.5 µm or less). The invention also provides a cutting instrument, comprising a cutting instrument body having two flat faces and a direction of elongation, and having at least one cutting edge extending parallel to the direction of elongation, wherein a maximum deviation from a line defined by two points on the ultimate edge of the cutting edge separated by 750 µm of any point on the ultimate edge of the cutting edge between the two points is about 1 µm or less (e.g., about 0.9 µm or less, or about 0.8 µm or less, even about 0.7 µm or less).

The following example further illustrates the invention but, of course, should not be construed as in any way limiting its scope.

EXAMPLE

A commercially available surgical blade made of carbon steel was examined by scanning electron microscopy at 5000-fold magnification at three points along the cutting edge, namely, the left side, the center, and the right side of the edge on both (i.e., the opposing) planar surfaces ("Surface A" and "Surface B") of the blade, for a total of six observations. The observations were made in a direction perpendicular to the plane defined by the blade.

The blade was then subjected to chemical-mechanical polishing with a commercially available polishing composition comprising silica, hydrogen peroxide, and water (Cabot Microelectronics Semi-Sperse W-2000 polishing composition), using a conventional CMP tool equipped with a concentric grooved CMP pad. The blade was held at a 17° angle relative to the polishing pad in a stationary carrier, and the CMP pad contacted the blade while rotating. The blade was polished for about 5 minutes per side and with a downforce of 6.4 kg. The blade was then examined by scanning electron microscopy as described above.

Measurements were made on both scanning electron micrographs at each of the six positions for the commercially available surgical blade before polishing in accordance with the inventive method ("control") and after polishing in accordance with the inventive method ("inv."). Lines were drawn between sets of two arbitrary endpoints 5000 µm, 750 µm, and 10 µm apart (the "feature width") on the ultimate edge of the cutting edge. A determination was made of the maximum deviation between (a) the aforementioned lines between the arbitrary endpoints and (b) any point on the ultimate edge of the cutting edge and between the arbitrary endpoints of the aforementioned lines. The percent change between the corresponding control and invention maximum deviation values was calculated as follows: $\Delta = 100 \times (\text{control} - \text{inv.})/\text{control}$. The results are set forth in Tables 1–3.

TABLE 1

5000 µm Feature Width

| 5000 µm Feature Width | Left Side Maximum Deviation (µm) | | | Center Maximum Deviation (µm) | | | Right Side Maximum Deviation (µm) | | |
|---|---|---|---|---|---|---|---|---|---|
| | Control | Inv. | Δ | Control | Inv. | Δ | Control | Inv. | Δ |
| Surface A | 5.5 | 3 | 45% | 6 | 3.5 | 42% | 5 | 2 | 60% |
| Surface B | 5 | 1.5 | 70% | 7 | 1.5 | 79% | 6.5 | 5 | 57% |

TABLE 2

750 µm Feature Width

| 750 µm Feature Width | Left Side Maximum Deviation (µm) | | | Center Maximum Deviation (µm) | | | Right Side Maximum Deviation (µm) | | |
|---|---|---|---|---|---|---|---|---|---|
| | Control | Inv. | Δ | Control | Inv. | Δ | Control | Inv. | Δ |
| Surface A | 2 | 1 | 50% | 3.5 | 1 | 71% | 4 | 1 | 75% |
| Surface B | 3 | 0.5 | 83% | 4 | 0.3 | 93% | 3 | 0 | 100% |

TABLE 3

10 µm Feature Width

| 10 µm Feature Width | Left Side Maximum Deviation (µm) | | | Center Maximum Deviation (µm) | | | Right Side Maximum Deviation (µm) | | |
|---|---|---|---|---|---|---|---|---|---|
| | Control | Inv. | Δ | Control | Inv. | Δ | Control | Inv. | Δ |
| Surface A | 1.5 | 0 | 100% | 1.5 | 0 | 100% | 1.5 | 0 | 100% |
| Surface B | 2 | 0 | 100% | 2 | 0 | 100% | 2 | 0 | 100% |

As is apparent from the results set forth in Tables 1–3, the maximum deviation in the ultimate edge of the cutting edge for the conventional surgical blade at all measuring sites was 5 μm or greater at a 5000 μm feature width (Table 1), 2 μm or greater at a 750 μm feature width (Table 2), and 1.5 μm or greater at a 10 μm feature width (Table 3). The maximum deviation in the ultimate edge of the cutting edge for the surgical blade after polishing in accordance with the inventive method was 3.5 μm or less at a 5000 μm feature width (Table 1), 1 μm or less at a 750 μm feature width (Table 2), and not detectable at a 10 μm feature width (Table 3). Thus, the invention provided an ultimate edge with an improved maximum deviation at a 5000 μm feature width of at least about 42% an improved maximum deviation at a 750 μm feature width of at least about 50%, and an improved maximum deviation at a 10 μm feature of about 100%.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method for polishing a cutting edge on a cutting instrument, comprising:
   (i) providing a cutting instrument having a cutting edge,
   (ii) contacting the cutting edge with a polishing pad and a chemical-mechanical polishing composition comprising:
      (a) particles of an abrasive,
      (b) an oxidizing agent, and
      (c) a liquid carrier,
      wherein the abrasive is suspended in the liquid carrier,
   (iii) moving the polishing pad relative to the cutting edge with the chemical-mechanical polishing composition therebetween, and
   (iv) abrading at least a portion of the cutting edge to polish the cutting edge.

2. The method of claim 1, wherein the abrasive is selected from the group consisting of silica, alumina, ceria, titania, zirconia, germania, diamond, polycarbonate, silicon carbide, titanium carbide, titanium nitride, niobium carbide, chromium carbide, and mixtures thereof.

3. The method of claim 2, wherein the abrasive is silica.

4. The method of claim 1, wherein the oxidizing agent is selected from the group consisting of bromates, bromites, chlorates, chlorites, ferric nitrate, hydrogen peroxide, hypochlorites, iodates, monoperoxy sulfate, monoperoxy sulfite, monoperoxyphosphate, monoperoxyhypophosphate, monoperoxypyorphosphate, organo-halo-oxy compounds, periodates, permanganate, and peroxyacetic acid.

5. The method of claim 1, wherein the cutting edge comprises a metal.

6. The method of claim 5, wherein the metal comprises an alloy of iron with at least one element selected from the group consist of carbon, chromium, nickel, and cobalt.

7. The method of claim 5, wherein the metal comprises a bulk amorphous alloy.

8. The method of claim 1, wherein the cutting edge comprises diamond.

9. The method of claim 1, wherein the cutting edge comprises sapphire.

10. The method of claim 1, wherein the liquid carrier is water.

11. The method of claim 1, wherein the cutting instrument is a knife.

12. The method of claim 11, wherein the knife is a surgical scalpel.

13. The method of claim 1, further comprising a step (v) of coating the cutting edge with a protective and/or strengthening coating.

14. The method of claim 1, wherein
   (a) the abrasive is selected from the group consisting of silica, alumina, ceria, titania, zirconia, germania, diamond, polycarbonate, silicon carbide, titanium carbide, titanium nitride, niobium carbide, chromium carbide, and mixtures thereof,
   (b) the liquid carrier is water, and
   (c) the polishing composition comprises an oxidizing agent selected from the group consisting of bromates, bromites, chlorates, chlorites ferric nitrate, hydrogen peroxide, hypochlorites, iodates, monoperoxy sulfate, monoperoxy sulfite, monoperoxyphosphate, monoperoxyhypophosphate monoperoxypyorphosphate, organo-halo-oxy compounds, periodates, permanganate, and peroxyacetic acid.

15. The method of claim 14, wherein the abrasive is silica, and the oxidizing agent is hydrogen peroxide.

16. A cutting instrument comprising a cutting edge produced by the method of claim 1.

17. The cutting instrument of claim 16, wherein the cutting instrument is a surgical scalpel.

18. A cutting instrument comprising a cutting instrument body having two flat faces and a direction of elongation, and having at least one cutting edge extending parallel to the direction of elongation and defining an ultimate edge, wherein a maximum deviation from a line defined by two points on the ultimate edge of the cutting edge separated by 5000 μm of any point on the cutting edge between the two points is about 4 μm or less.

19. The cutting instrument of claim 18, wherein the cutting instrument body comprises an alloy of iron with at least one element selected from the group consisting of carbon, chromium, nickel, and cobalt.

20. A cutting instrument, comprising a cutting instrument body having two flat faces and a direction of elongation and defining an ultimate edge, and having at least one cutting edge extending parallel to the direction of elongation, wherein a maximum deviation from a line defined by two points on the ultimate edge of the cutting edge separated by 750 μm of any point on the cutting edge between the two points is about 1 μm or less.

21. The cutting instrument of claim 20, wherein the cutting instrument body comprises an alloy of iron with at least one element selected from the group consisting of carbon, chromium, nickel, and cobalt.

* * * * *